United States Patent
Mori et al.

(10) Patent No.: US 9,891,241 B2
(45) Date of Patent: Feb. 13, 2018

(54) AUTOMATIC ANALYSIS DEVICE

(71) Applicant: HITACHI HIGH-TECHNOLOGIES CORPORATION, Tokyo (JP)

(72) Inventors: Takamichi Mori, Tokyo (JP); Kazuhiro Nakamura, Tokyo (JP); Yoshihiro Suzuki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/760,818

(22) PCT Filed: Jan. 17, 2014

(86) PCT No.: PCT/JP2014/050823
§ 371 (c)(1),
(2) Date: Jul. 14, 2015

(87) PCT Pub. No.: WO2014/112591
PCT Pub. Date: Jul. 24, 2014

(65) Prior Publication Data
US 2015/0346231 A1    Dec. 3, 2015

(30) Foreign Application Priority Data
Jan. 21, 2013 (JP) .................................. 2013-008635

(51) Int. Cl.
G01N 35/10 (2006.01)

(52) U.S. Cl.
CPC ..... G01N 35/1004 (2013.01); G01N 35/1002 (2013.01); G01N 35/1011 (2013.01)

(58) Field of Classification Search
CPC ................................................ G01N 35/1004
See application file for complete search history.

(56) References Cited

U.S. PATENT DOCUMENTS

| 3,552,212 A | 1/1971 | Ohlin |
| 3,719,086 A | 3/1973 | Bannister et al. |

(Continued)

FOREIGN PATENT DOCUMENTS

| EP | 0 539 994 A2 | 5/1993 |
| JP | 53-57893 U | 5/1978 |

(Continued)

OTHER PUBLICATIONS

English translation of JP2001133466, Toshiba Corp, Published May 18, 2001, pp. 1-11.*

(Continued)

*Primary Examiner* — P. Kathryn Wright
(74) *Attorney, Agent, or Firm* — Mattingly & Malur, PC

(57) ABSTRACT

An automatic analysis device in which a probe is washed in a short period of time and the amount of washing water which may be mixed in at the time of suctioning of a succeeding liquid can be decreased. Washing water is supplied to a throttle portion of a washing tank from a washing nozzle. A reagent probe is inserted into the washing tank. Washing of the outside of the reagent probe, washing of the throttle portion, and a washing operation for the inside of the reagent probe are performed while a lowering operation of the reagent probe is performed. The automatic analysis device is configured to perform a drying operation by using vacuum nozzles even when the reagent probe is lifted, and thus, washing and drying operations of the reagent probe can be sped up and can be performed in a short period of time.

8 Claims, 14 Drawing Sheets

(56) References Cited

U.S. PATENT DOCUMENTS

| | | | | |
|---|---|---|---|---|
| 5,279,794 A * | 1/1994 | Sasao | ............... | G01N 35/1004 134/140 |
| 2005/0074363 A1 | 4/2005 | Dunfee | | |
| 2005/0279387 A1* | 12/2005 | Blackwell | .......... | G01N 35/1004 134/22.1 |

FOREIGN PATENT DOCUMENTS

| | | |
|---|---|---|
| JP | 4-105066 A | 4/1992 |
| JP | 2001-133466 A | 5/2001 |
| JP | 2002-340913 A | 11/2002 |
| JP | 2006-257491 A | 9/2006 |
| WO | 2011/062982 A1 | 5/2011 |

OTHER PUBLICATIONS

International Preliminary Report on Patentability received in corresponding International Application No. PCT/JP2014/050823 dated Jul. 30, 2015.
Communication Pursuant to Rule 164(1) EPC received in corresponding European Application No. 14740134.3 dated Sep. 12, 2016.
International Search Report of PCT/JP2014/050823.
Chinese Office Action received in corresponding Chinese Application No. 201480004368.3 dated Nov. 3, 2016.

\* cited by examiner

[Fig. 1]
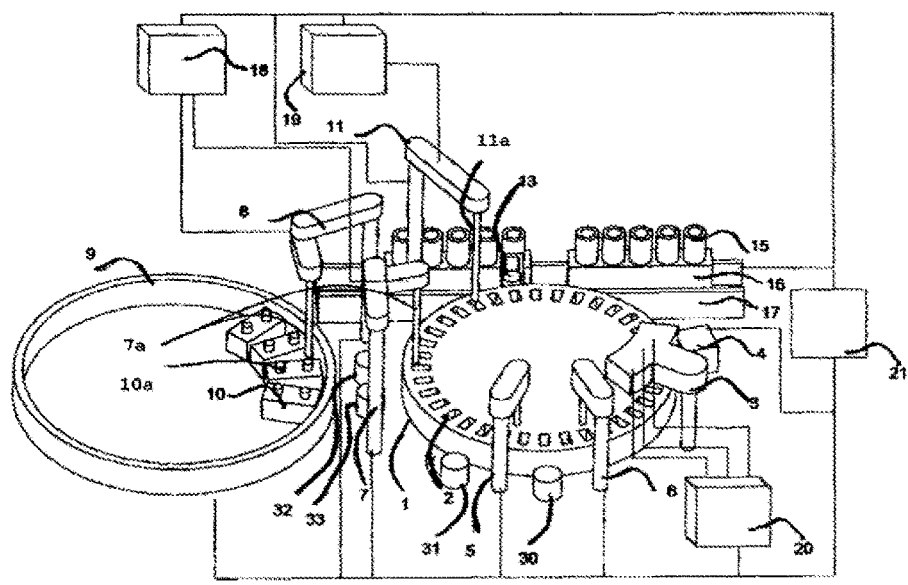

[Fig. 2A]
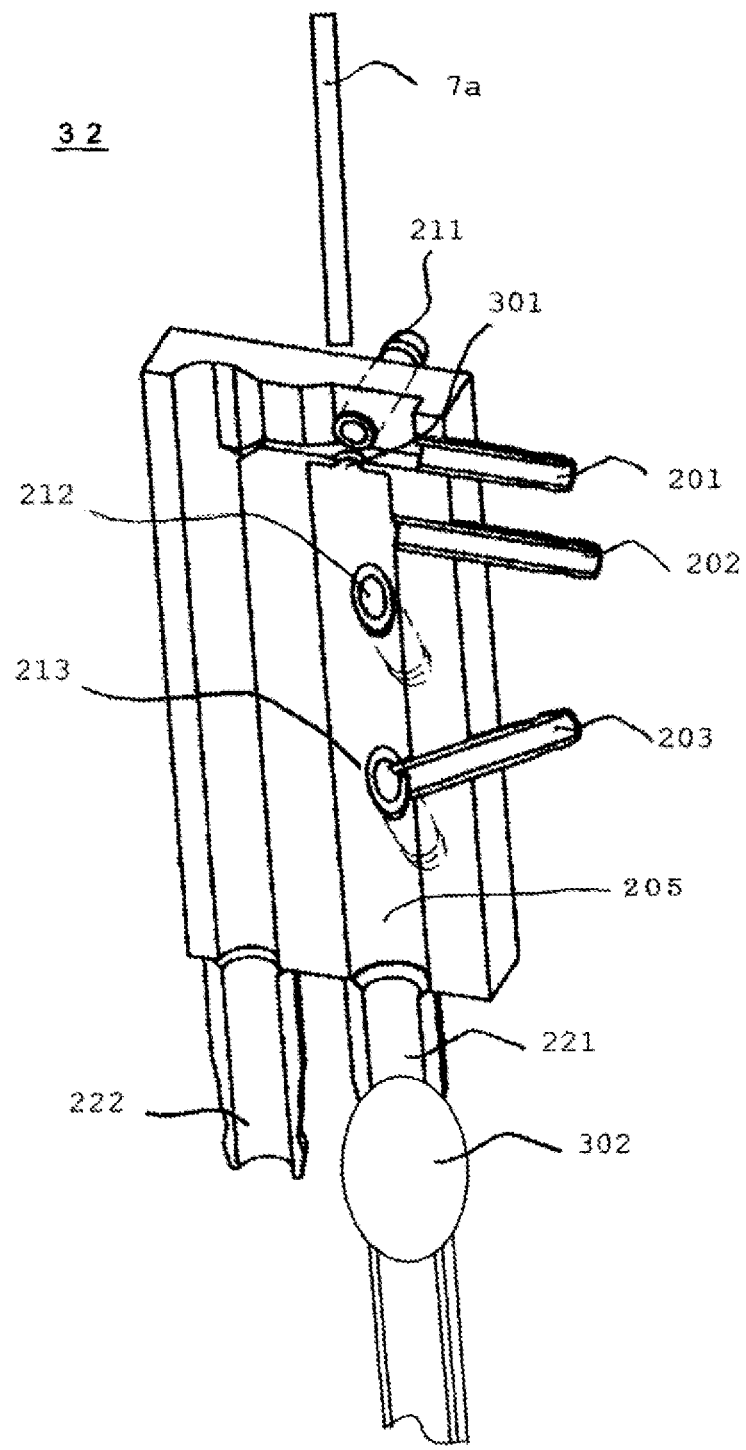

[Fig. 2B]
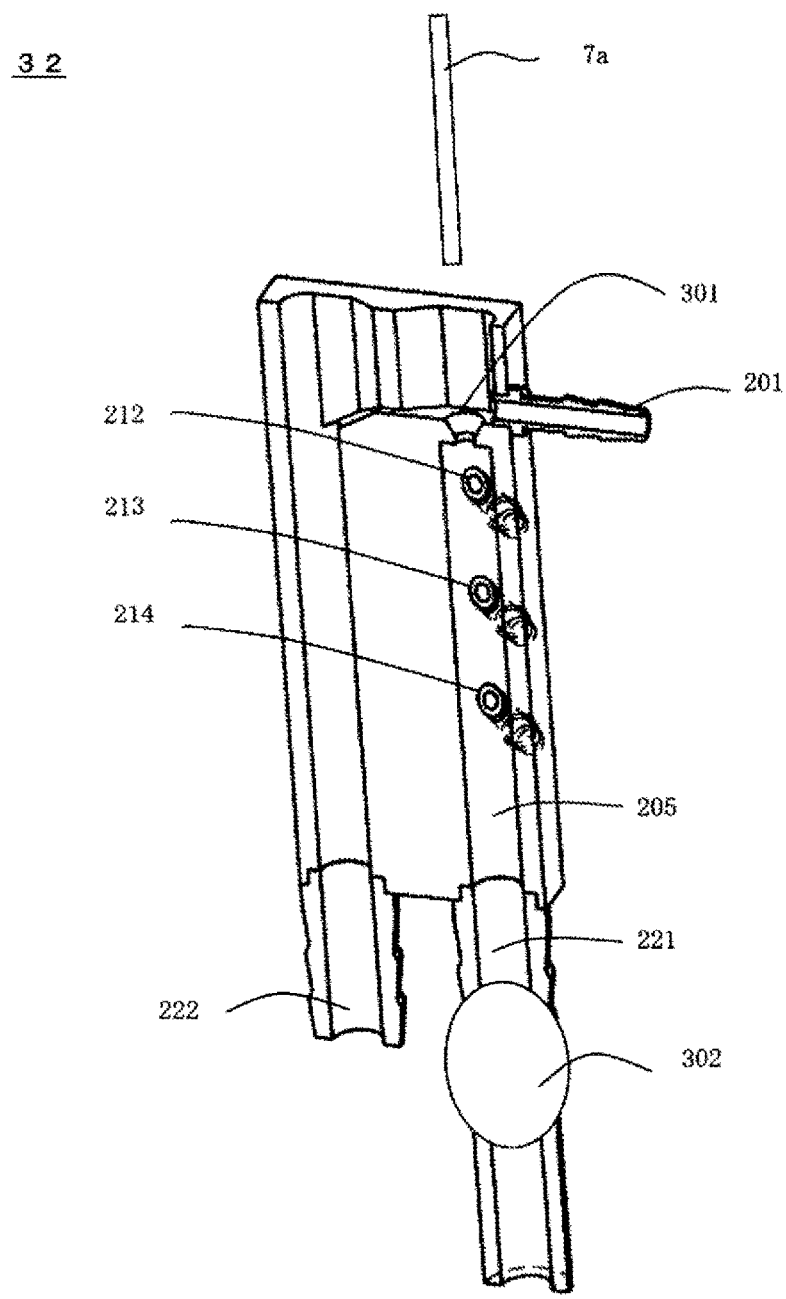

[Fig. 3A]
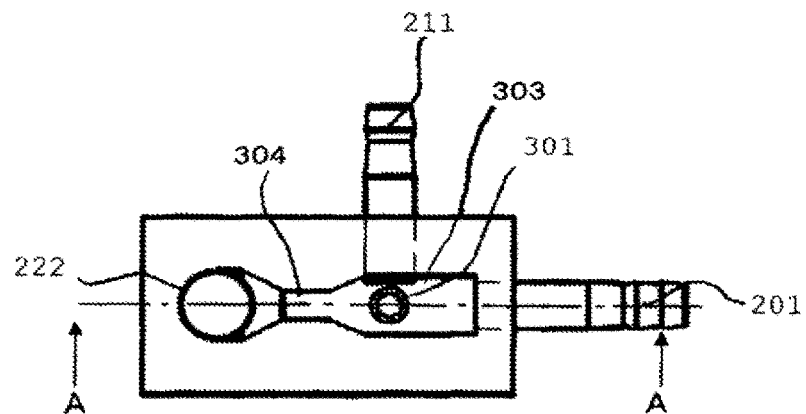
[Fig. 3B]
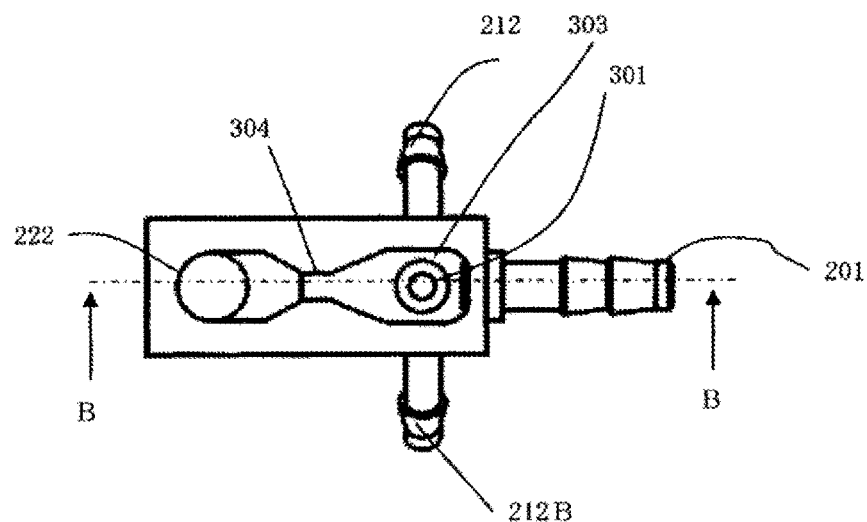

[Fig. 3C]
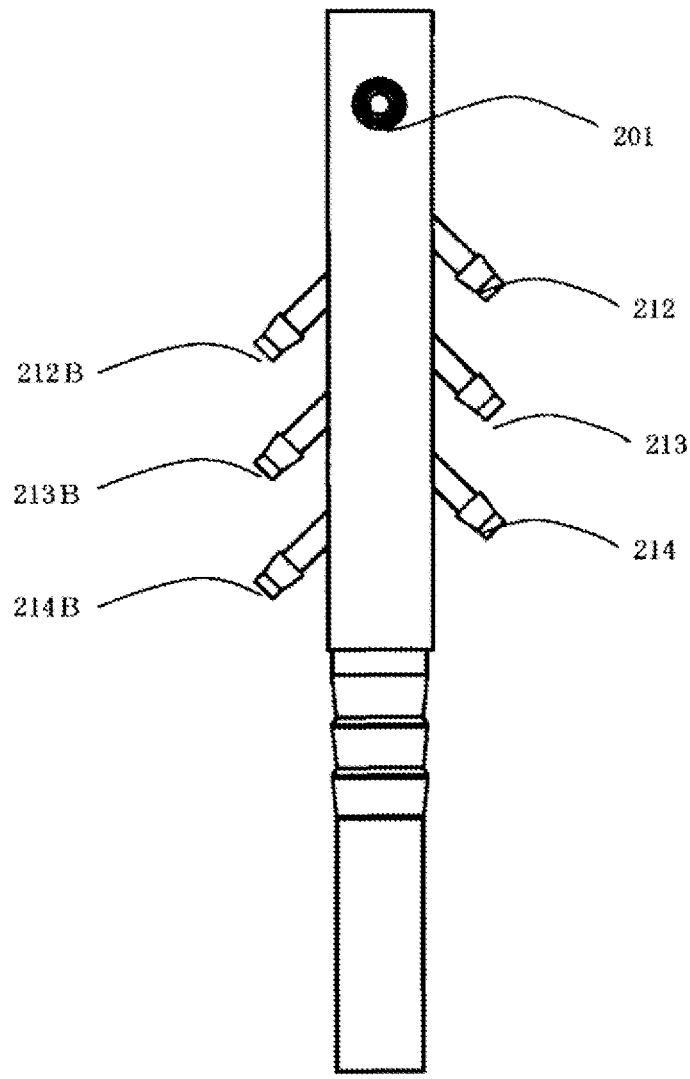

[Fig. 4]
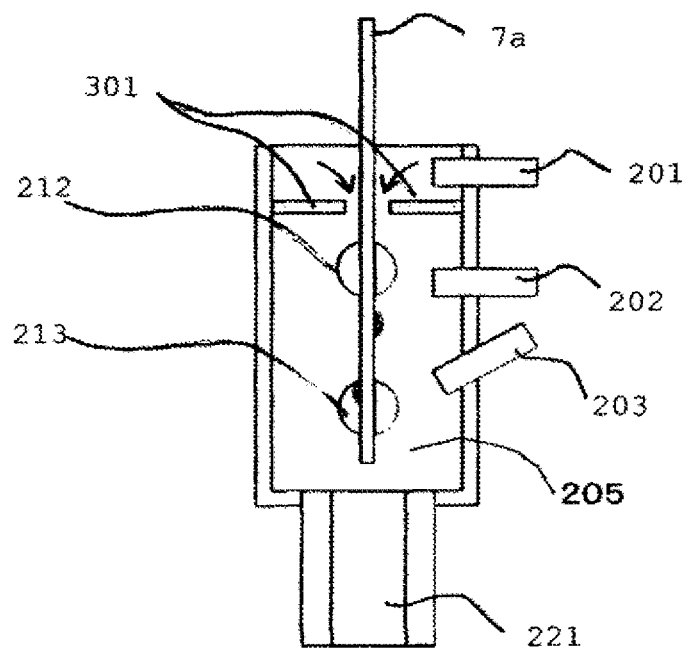

[Fig. 5]
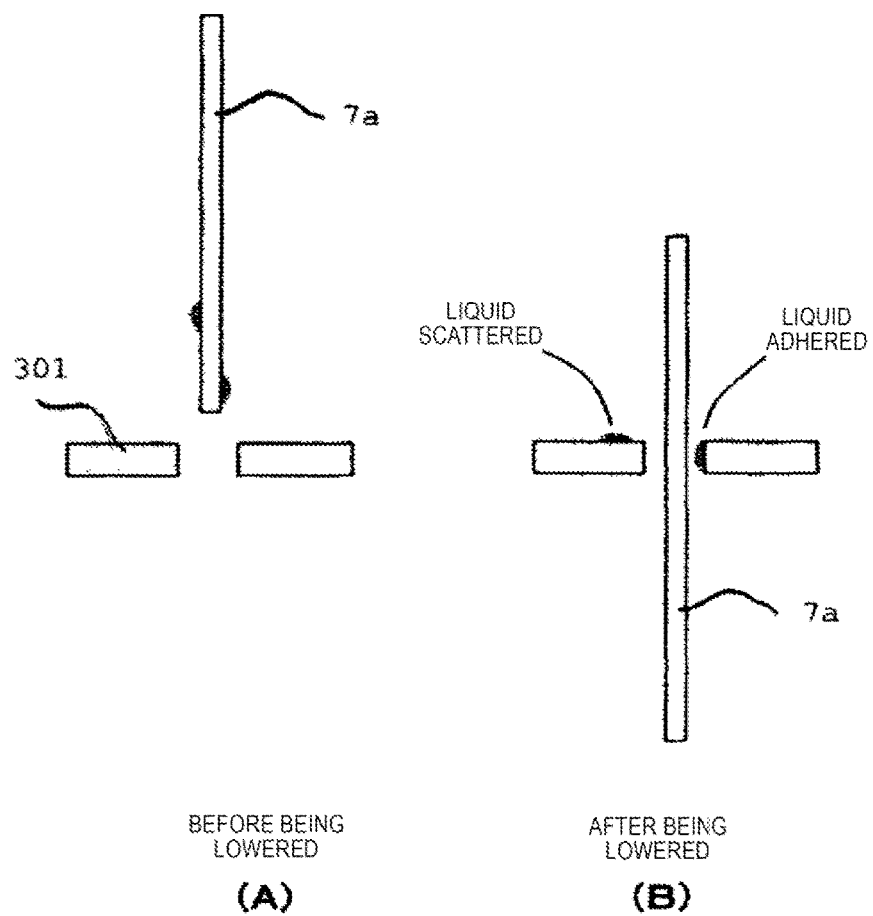
BEFORE BEING LOWERED
(A)
AFTER BEING LOWERED
(B)

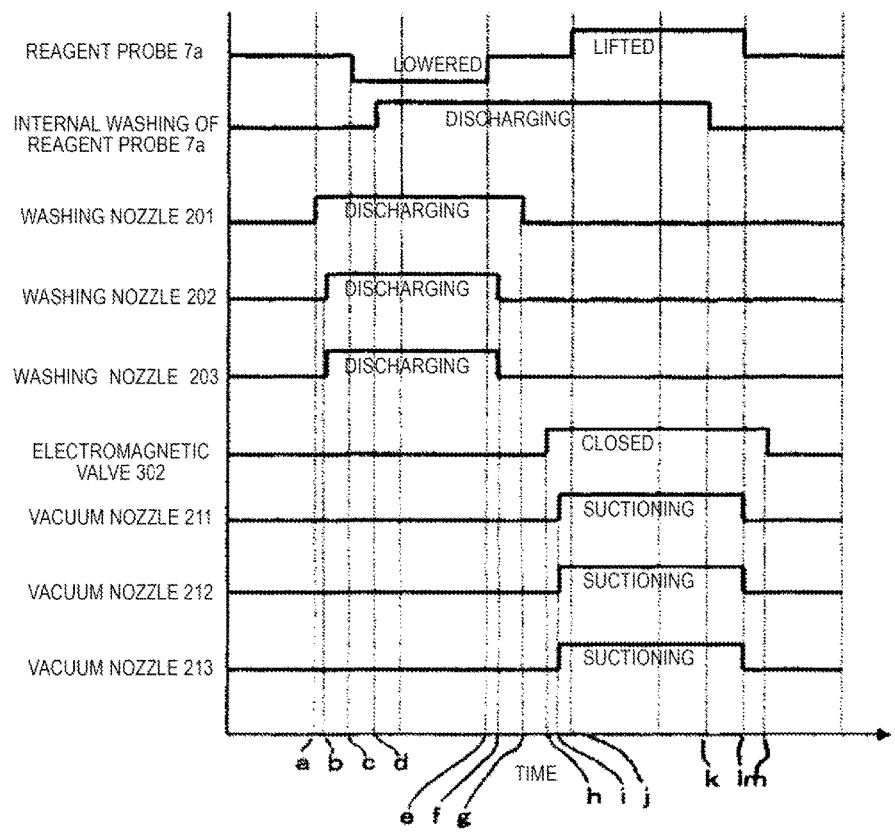
[Fig. 6A]

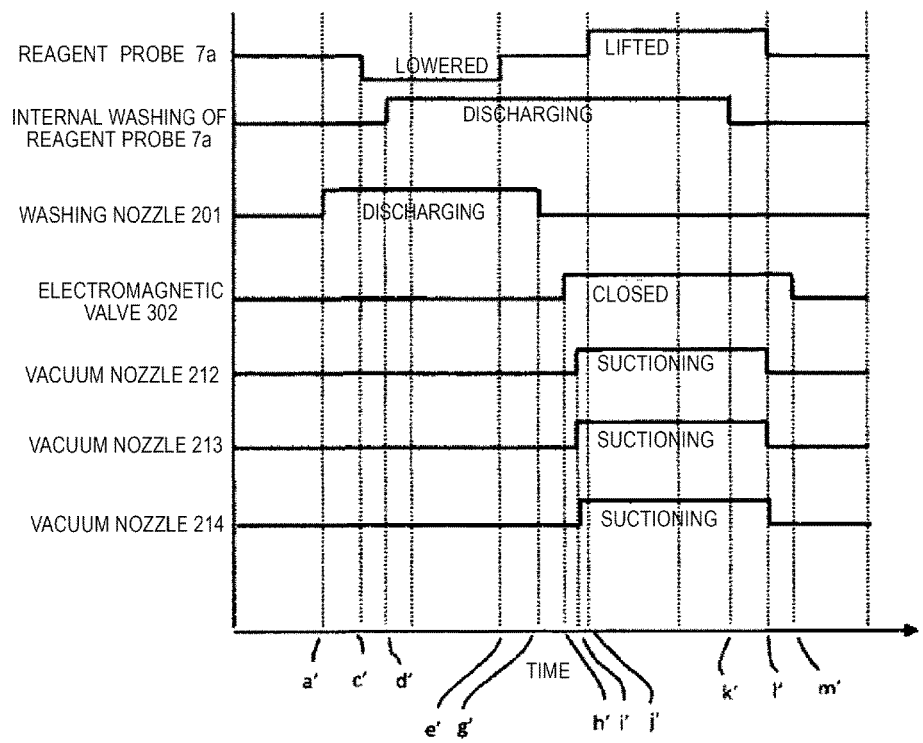
[Fig. 6B]

[Fig. 7]
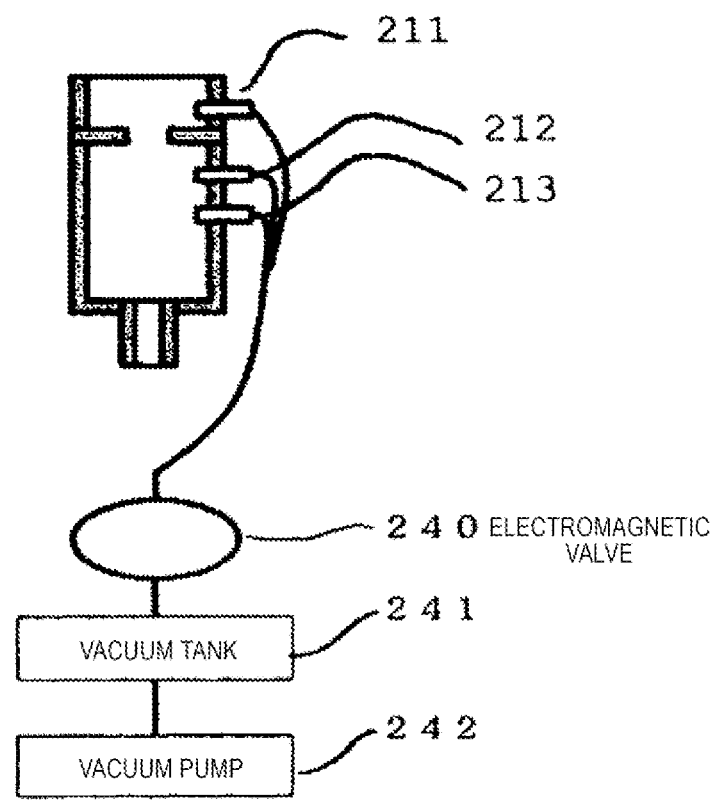

[Fig. 8]
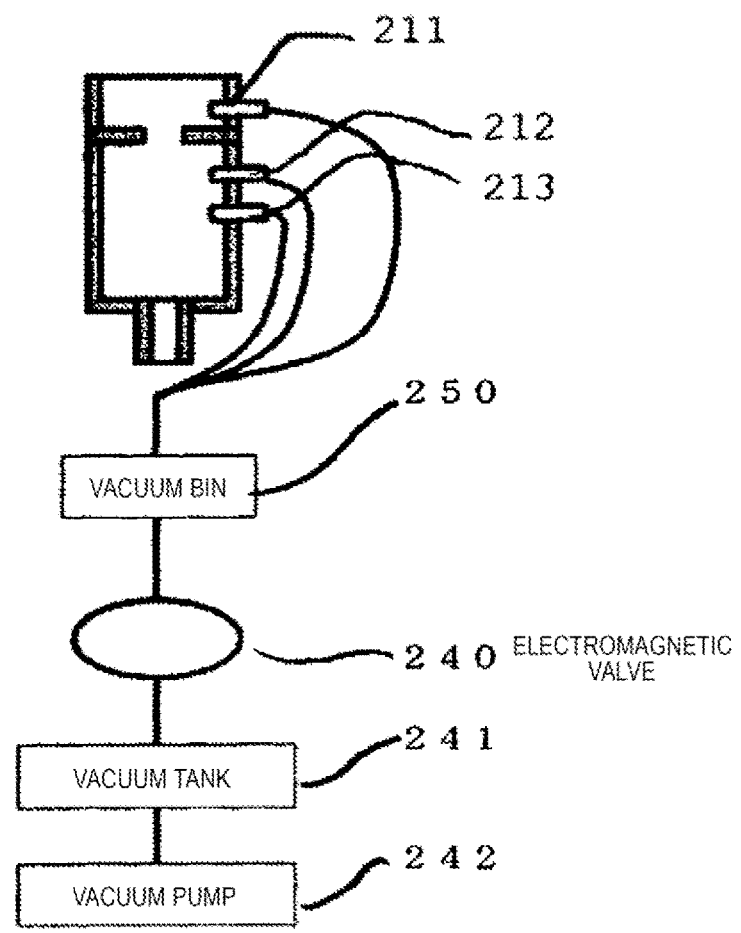

[Fig. 9]
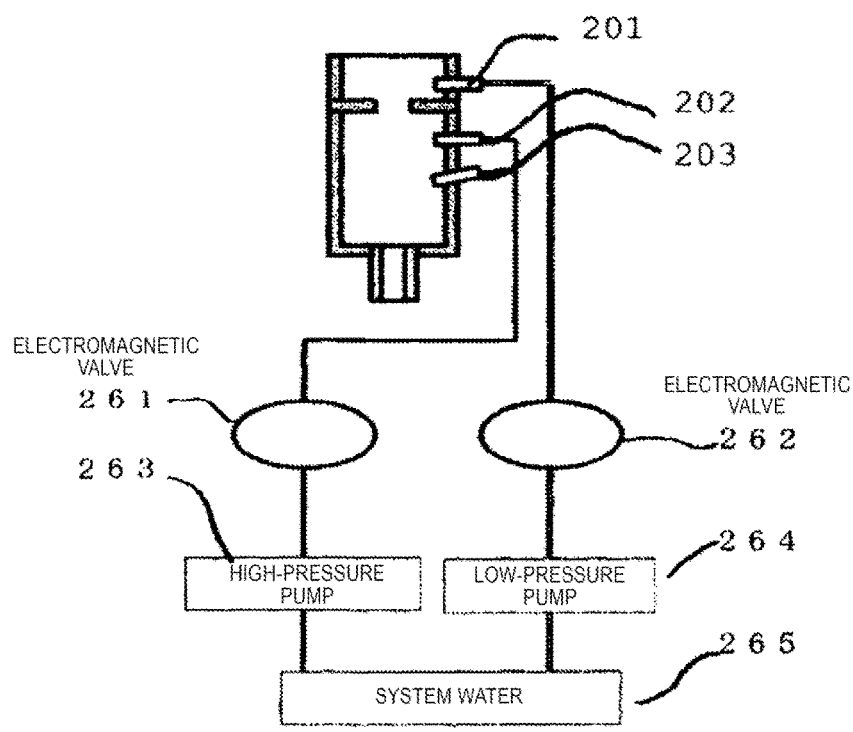

[Fig. 10]
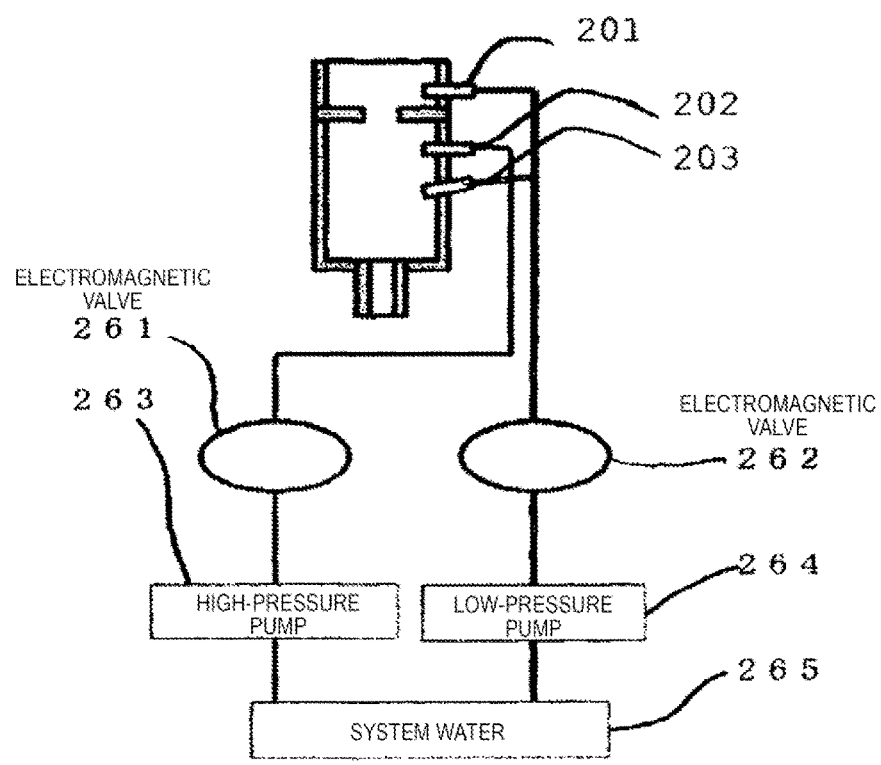

[Fig. 11]
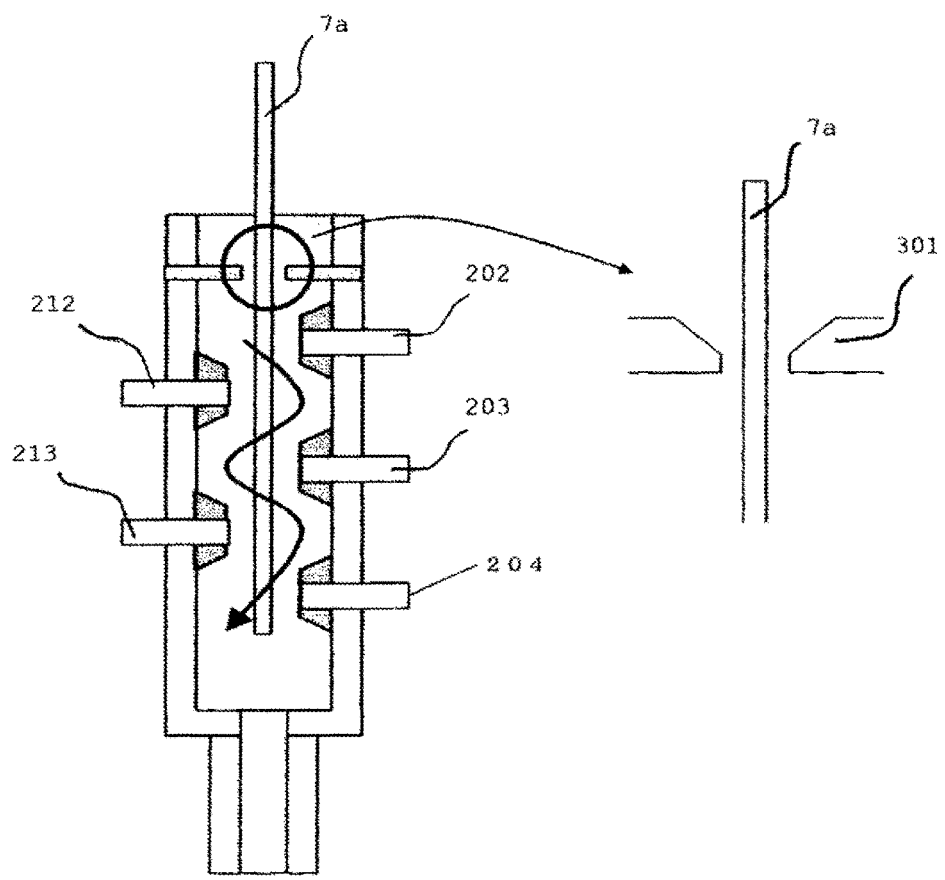

AUTOMATIC ANALYSIS DEVICE

TECHNICAL FIELD

The present invention relates to an automatic analysis device which analyzes a reagent and a liquid sample such as blood or urine.

BACKGROUND ART

For example, an automatic analysis device such as an automatic biochemical analyzer and an automatic immunoassay analyzer includes a washing tank for washing a probe with washing water after suctioning and discharging a reagent or a target specimen sample.

Generally, a level of contamination of the probe during suctioning of the reagent or the target specimen sample performed by using the probe is in a volume range of approximately 5 mm in which the probe is thrust into the reagent or the sample after the probe detects the liquid surface. Therefore, the range becomes a washing range of the probe. However, for example, in order to prevent evaporation of the reagent, when suctioning the reagent through the probe from a notched reagent bottle attached with a cap, the probe needs to be washed over a wide range corresponding to the range from the cap of the reagent to the bottom of the reagent bottle.

However, widening of the washing range of the probe results in a disadvantage described below. First, as the washing range is widened, a washing time needs to be sufficiently provided. In addition, after the probe is washed, a large quantity of washing water adhered onto a side surface of the probe remains. If a succeeding reagent is suctioned through the probe in such a state, it is assumed that the washing water adhered onto the side surface of the probe is mixed in the reagent bottle, thereby leading to dilution of the reagent caused by washing water.

Even in a case where the probe is thrust deep inside the target specimen sample, as described above, an equivalent disadvantage is caused due to the wide washing range of the probe.

Therefore, when the washing range of the probe is wide (example: a washing range of 80 mm), as a method of removing washing water adhered onto the side surface of the probe after the probe is washed, there is a known method of removing washing water adhered onto the side surface of the probe by moving the probe to a position of a vacuum suctioning tube after being washed at a probe washing position, lowering the probe into the vacuum suctioning tube, and evacuating the inside of the vacuum suctioning tube (PTL 1 and PTL 2).

CITATION LIST

Patent Literature

PTL 1: JP-A-2002-340913
PTL 2: JP-A-2006-257491

SUMMARY OF INVENTION

Technical Problem

According to the technologies disclosed PTL 1 and PTL 2, since a washed probe moves to the top surface of a vacuum suctioning tube, there is no contamination in the vicinity of a vacuum suctioning port caused by a reagent adhered onto the probe, a target specimen sample, and washing water scattered during washing of the probe.

Here, there is a demand for a quicker operation in an automatic analysis device and minimization of an installation space for a washing tank. In this case, it is considered to execute processes of the probe from washing to drying in the same washing tank, to speed up a washing operation, and to minimize the installation space.

In this case, considering an improvement of efficiency in removing washing water adhered onto the probe during vacuum suctioning, it is considered to narrow an opening portion of the washing tank.

However, when the hole diameter of the opening portion of the washing tank is decreased, there is a significant possibility that the reagent or the target specimen sample adhered onto the probe when the probe is lowered into the washing tank before being washed may scatter or adhere onto the vicinity of the opening portion of the washing tank. As the probe is inserted into the washing tank, there is a high risk in that the vicinity of the opening portion of the washing tank is contaminated by the reagent or the target specimen sample scattered or adhered, and when the probe is lifted in order to dry the probe after being washed in the washing tank, the probe comes into contact with a liquid scattered or adhered onto the vicinity of the opening portion of the washing tank, thereby causing contamination during suctioning of a succeeding liquid.

An object of the present invention is to realize an automatic analysis device in which a washing effect of a probe is improved by being washed in a short period of time and washing water and the like which may be mixed in during suctioning of a succeeding liquid can be decreased.

Solution to Problem

The following is a configuration of the present invention for achieving the aforementioned objects.

According to a representative aspect of the invention, there is provided an automatic analysis device including: a probe that suctions a reagent or a sample and discharges the reagent or the sample into a reaction container; a dispensing mechanism that moves the probe vertically and horizontally; a suctioning and discharging mechanism that causes the probe to suction the reagent or the sample and discharges the reagent or the sample into the reaction container; a photometer that analyzes the sample in the reaction container; a throttle portion that forms an opening portion into which the probe is inserted; a washing mechanism that discharges washing water which flows on a top surface of the throttle portion;

a drying mechanism that is arranged below the throttle portion and performs vacuum suctioning of washing water; and a controller that controls operations of the dispensing mechanism, the suctioning and discharging mechanism, the washing mechanism, and the drying mechanism.

In addition, in an automatic analysis device, a washing tank for washing a probe that suctions a reagent or a sample and discharges the reagent and the sample to a reaction container includes a throttle portion forming an opening portion into which the probe is inserted, a first washing and drying mechanism being arranged near the throttle portion and performing discharging and vacuum suctioning of washing water, a washing portion being formed below the throttle portion, and a second washing and drying mechanism being connected to the washing portion and performing discharging and vacuum suctioning of washing water. Processes of the probe from washing to drying are performed in the same washing tank.

Advantageous Effects of Invention

According to the present invention, it is possible to realize an automatic analysis device in which a washing effect of a probe is improved by being washed in a short period of time and washing water and the like which may be mixed in during suctioning of a succeeding liquid can be decreased.

BRIEF DESCRIPTION OF DRAWINGS

FIG. 1 is a diagram of a schematic configuration of an automatic analysis device to which the present invention is applied.

FIG. 2A is a perspective cross-sectional view of a washing tank according to an exemplary embodiment of the present invention.

FIG. 2B is a perspective cross-sectional view of the washing tank according to another exemplary embodiment of the present invention.

FIG. 3A is a top view of the washing tank.

FIG. 3B is another top view of the washing tank.

FIG. 3C is a side view of the washing tank.

FIG. 4 is an explanatory diagram of a configuration of the washing tank.

FIG. 5A is another explanatory diagram of the configuration of the washing tank.

FIG. 5B is another explanatory diagram of the configuration of the washing tank.

FIG. 6A is a time chart of an operation of washing a reagent probe.

FIG. 6B is a time chart of another operation of washing the reagent probe.

FIG. 7 is a diagram illustrating an example of a mechanism for performing operations of suctioning vacuum nozzles.

FIG. 8 is a diagram illustrating another example of the mechanism for performing operations of suctioning the vacuum nozzles.

FIG. 9 is a diagram illustrating an example of a mechanism for performing operations of discharging washing water through washing nozzles.

FIG. 10 is a diagram illustrating another example of the mechanism for performing operations of discharging washing water through the washing nozzle.

FIG. 11 is a diagram illustrating a modification example of the washing tank.

DESCRIPTION OF EMBODIMENTS

Hereinafter, an exemplary embodiment of the present invention will be described with reference to the drawings.

Exemplary Embodiment

FIG. 1 is a diagram of a schematic configuration of an automatic analysis device to which the present invention is applied.

In FIG. 1, reaction containers 2 are arranged on the circumference of a reaction disk 1. A plurality of reagent bottles 10 can be arranged on the circumference of a reagent disk 9. In addition, detergent bottles 10a can be arranged in the reagent disk 9. A sample transportation mechanism 17 for moving a rack 16 mounted with sample containers 15 is installed near the reaction disk 1.

Reagent dispensing mechanisms 7 and 8 which can rotate and vertically move are installed between the reaction disk 1 and the reagent disk 9, and each of the reagent dispensing mechanisms 7 and 8 includes a reagent probe 7a. The reagent probe 7a moves vertically and horizontally by the reagent dispensing mechanism 7 or 8. Reagent syringes 18 (suctioning and discharging mechanisms) are respectively connected to the reagent probes 7a. The reagent syringes 18 suctions and discharges a reagent through the reagent probes 7a. In addition, the reagent syringes 18 discharges washing water into the reagent probe 7a and suctions washing water or detergent from the detergent bottle 10a, thereby washing the inside of the reagent probe 7a.

In addition, a sample dispensing mechanism 11 which can rotate and vertically move is installed between the reaction disk 1 and the sample transportation mechanism 17, and the sample dispensing mechanism 11 includes a sample probe 11a. Each of sample syringes 19 are connected to the sample probe 11a. The sample probe 11a moves horizontally in an arc while being centered around the rotary axis. The sample probe 11a moves vertically so as to dispense sample from a sample container to the reaction container 2.

In the periphery of the reaction disk 1, a washing mechanism 3, a spectrophotometer 4 for analyzing a sample in the reaction container 2, stirring mechanisms 5 and 6, the reagent disk 9, and the sample transportation mechanism 17 are arranged. A washing pump 20 is connected to the washing mechanism 3. Washing tanks 13, 30, 31, 32, and 33 are respectively arranged above the operation range of the reagent dispensing mechanisms 7 and 8, the sample dispensing mechanism 11, the stirring mechanisms 5 and 6. The washing tank 13 is a washing tank for the sample probe 11a, and the washing tanks 30 and 31 are washing tanks for the stirring mechanisms 5 and 6. Then, the washing tanks 32 and 33 are washing tanks for the reagent probe 7a and the reagent dispensing probe of the reagent dispensing mechanism 8.

The sample container 15 contains an inspection sample such as blood and is mounted on the rack 16, thereby being carried by the sample transportation mechanism 17. In addition, each of the mechanisms is connected to a controller 21, and operational control thereof is performed by the controller 21.

A cap is attached to a position of a reagent probe suctioning port of the reagent bottle 10 in order to seal the inside thereof. Generally, the cap is detached when the reagent bottle 10 is set in the automatic analysis device, and then, the reagent bottle 10 is installed in the device. However, recently, there is provided a method in which a notch-like hole is bored in the cap and the reagent probe 7a is inserted into a notch portion so as to suction a reagent. Since a slight notch becomes an opening portion of the cap for the reagent bottle 10, contact of the reagent with respect to the air outside is minimized, thereby improving deterioration of the reagent.

However, since a washing range of the reagent probe 7a becomes the overall range of the reagent probe 7a which is inserted through the cap of the reagent bottle 10 in order to suction a reagent, it is necessary to perform washing over a wide range compared to a case where the reagent bottle 10 includes no cap.

FIG. 2A is a perspective cross-sectional view of the washing tank 32 according to an exemplary embodiment of the present invention. The washing tank 32 is configured to include an electromagnetic valve 302 below a waste liquid portion 221. In addition, FIG. 3A is a top view of the washing tank 32. The cross section taken along line A-A in FIG. 3A is the cross section illustrated in FIG. 2A. The washing tank 32 is formed with the structure having the shape illustrated in FIG. 2A and another structure having a shape symmetrical to the illustrated structure. However, a suctioning nozzle 211 described-below is formed in only one structure therebetween. The washing tank 33 is also configured to be equivalent to the washing tank 32.

In FIGS. 2A and 3A, in order to wash the reagent probe 7a, the reagent probe 7a is lowered into the washing tank 32. Then, the reagent probe 7a passes through an opening portion 303 formed on the top surface of the washing tank 32, and a throttle portion 301 forming a circular opening, thereby being inserted into the washing tank 32. The circular opening is an opening (portion) through which the reagent probe 7a is inserted, and the opening (portion) is formed in the throttle portion 301. The opening (portion) is not necessarily circular.

Washing nozzles 202 and 203 are connected to the washing tank 32 so as to supply washing water to the inside of the washing tank 32. A channel throttle portion 304 is formed in the opening portion 303. The throttle portion 301 includes the opening portion 303 and forms a channel through which washing water discharged from a washing nozzle 201 flows in a horizontal direction. The washing nozzle 201 discharges washing water which flows on the top surface of the throttle portion 301. The channel width of the channel on a downstream side from an inlet port of the channel throttle portion 304 included in the throttle portion 301 is smaller than the channel width on an upstream side therefrom. It is acceptable that the channel width of the channel on the downstream side from the opening (portion) through which the reagent probe 7a is inserted is smaller than the channel width on the upstream side.

A washing portion 205 for washing the reagent probe is formed below from the opening portion 303. The washing nozzles 202 and 203 are connected to the washing portion 205.

Washing water is supplied from the washing nozzles 202 and 203 to the washing portion 205 inside the washing tank 32. The reagent probe 7a is washed by applying washing water to the reagent probe 7a. Meanwhile, the electromagnetic valve 302 is in an open state. Then, after being washed of the reagent probe 7a, the electromagnetic valve 302 below the waste liquid portion 221 is in a closed state. Then, vacuum nozzles 212 and 213 connected to the washing portion 205 of the washing tank 32 start vacuum suctioning, and the reagent probe 7a is lifted while performing vacuum suctioning.

The suctioning velocity of the air intruding into the washing tank 32 during vacuum suctioning performed through the vacuum nozzles 212 and 213 can be increased as the opening is throttled at the throttle portion 301. Washing water adhered to the reagent probe 7a is blown away through the throttle portion 301, and then, washing water can be removed. Here, if the diameter of the opening formed by the throttle portion 301 is excessively significant compared to the outer diameter of the reagent probe 7a, the air intruding into the washing tank 32 diminishes in velocity. Accordingly, an effect of blowing washing water adhered onto the side surface of the reagent probe 7a decreases, resulting in dilution caused by remaining washing water when performing suctioning of a succeeding liquid.

As a countermeasure therefor, as illustrated in FIG. 4, the size of the opening formed by the throttle 301 is decreased so that the intruding velocity of the air through the throttle portion 301 during vacuum suctioning can be increased.

When clearance between the outer diameter of the reagent probe 7a and the diameter of the hole (the diameter of the opening) formed by the throttle portion 301 is caused to range within 0.2 mmm to 1.0 mm, a drying effect of the reagent probe 7a increases. As an example, when the outer diameter of the reagent probe 7a is 2 mm, it is favorable that an optimum hole diameter of the throttle portion 301 ranges approximately within 2.4 mm to 4.0 mm.

However, as illustrated in FIG. 5(A), by narrowing the throttle portion 301, there is no liquid adhered to the throttle portion 301 before the reagent probe 7a passes through the throttle portion 301, but as illustrated in FIG. 5(B), there is a case where a liquid adhered to the reagent probe 7a adheres to the throttle portion 301 and the vicinity thereof after the reagent probe 7a passes through the throttle portion 301.

In a state where a liquid adheres to the throttle portion 301, when lifting the reagent probe 7a in order to remove washing water after being washed, the liquid adheres onto the side surface of the reagent probe 7a, and the liquid adhered to the probe 7a mixes in during suctioning of a succeeding liquid, thereby causing contamination.

As a countermeasure therefor, as illustrated in FIG. 2A, the washing nozzle 201 which communicates with an upper portion of the throttle portion 301 is connected to the washing tank 32, and then, a liquid which has scattered and adhered to the throttle portion 301 is subjected to perifusion washing with washing water supplied from the washing nozzle 201. The washing tank 32 is connected to the vacuum nozzles 212 and 213 which communicate with the inside of the washing tank 32, and the suctioning nozzle 211 which is connected to the vicinity of the throttle portion 301 on an outlet port side. After the throttle portion 301 is washed by using the washing nozzle 201, if the reagent probe 7a is lifted while performing suctioning through the vacuum nozzles 212 and 213 and the suctioning nozzle 211, the reagent probe 7a can be drawn out from the washing tank 301 allowing no liquid to adhere to the reagent probe 7a.

As a specific method of using the washing nozzle 201, as described above, after washing the reagent probe 7a through the washing nozzles 202 and 203, the throttle portion 301 is subjected to perifusion.

Otherwise, as illustrated in the time chart of FIG. 6A, washing water is discharged from the washing nozzle 201 before washing the reagent probe 7a. Next, while washing water is discharged from the washing nozzles 202 and 203, the washing water discharged from the washing nozzle 201 is applied to the reagent probe 7a, and the reagent probe 7a is lowered. Most liquids adhered to the reagent probe 7a are removed by the washing water discharged from the washing nozzle 201. In order to achieve a greater washing effect, washing is performed through the washing nozzles 202 and 203.

Here, with reference to the time chart of an operation of washing the reagent probe 7a illustrated in FIG. 6A, descriptions will be given regarding operations of the reagent probe 7a, the washing nozzles 201 to 203, the electromagnetic valve 302, the vacuum nozzles 212 and 213, and the suctioning nozzle (the vacuum nozzle) 211.

In FIG. 6A, at a time a, the washing nozzle 201 starts discharging of washing water. Subsequently, at a time b, the washing nozzles 202 and 203 start discharging of washing water. Next, at a time c, the reagent probe 7a starts being lowered toward the washing tank 32 so as to be inserted into the washing tank 32. Then, at a time d, washing water is discharged from the reagent probe 7a, thereby starting internal washing for washing the inside of the reagent probe 7a. The internal washing and external washing of the probe 7a are performed simultaneously.

Next, at a time e, an operation of lowering the reagent probe 7a stops. Thereafter, at a time f, the washing nozzles 202 and 203 stop discharging of washing water. Subsequently, at a time g, the washing nozzle 201 stops discharging of washing water.

Next, at a time h, the electromagnetic valve 302 is in the closed state, and at a time i, the vacuum nozzles 211, 212, and 213 start suctioning of the inside of the washing tank 32. Then, at a time j, an operation of lifting the reagent probe 7a starts. Subsequently, at a time k, an operation of washing the inside of the reagent probe 7a stops. At a time l, the operation of lifting the reagent probe 7a stops, and the vacuum nozzles 211, 212, and 213 stop suctioning of the inside of the washing tank 32. Then, at a time m, the electromagnetic valve 302 is in the open state.

The above-described operation is executed by a command from the controller 21 in accordance with a program stored in the controller 21.

It is possible to adopt a method in which washing water discharged from the washing nozzles 202 and 203 is applied to the reagent probe 7a at the high-pressure flow velocity. Regarding washing water discharged from the washing nozzle 201, since the diameter of the throttle portion 301 is minimized, most of the washing water discharged from the washing nozzle 201 passes through the throttle portion 301 so as to flow down into an overflow portion 222 without dripping from the throttle portion 301. Since washing water discharged from the washing nozzle 201 flows so as to form a lid without dripping from the throttle portion 301, there is no need to be concerned about scattering of washing water discharged from the washing nozzles 202 and 203, and scattering from the throttle portion 301 to the upper portion.

In addition, since washing water discharged from the washing nozzle 201 plays a role as a lid with respect to the throttle portion 301, while the distal end of the reagent probe 7a is positioned lower than the throttle portion 301, washing water for washing the inside of the reagent probe 7a does not scatter from the throttle portion 301. In addition, while the reagent probe 7a is lifted, the inside of the washing tank 32 is subjected to vacuum suctioning by the vacuum nozzles 211, 212, and 213, and thus, the air is in a flow intruding into the washing tank 32 with respect to the throttle portion 301. Accordingly, the inside of the reagent probe 7a can be washed for a long period of time from the lowering of the probe 7a to the lifting thereof, and thus, the reagent probe 7a can be effectively washed.

Here, there is a slight time difference between a time at which the washing nozzles 201, 202, and 203 stop an operation of discharging washing water and a time at which the vacuum nozzles 211, 212, and 213 start a suctioning operation. However, since the sample probe 7a is lowered into the washing tank 32 and stops thereat, a washing liquid discharged from the distal end of the sample probe 7a does not scatter from the throttle portion 301. Naturally, a vacuum suctioning operation may be immediately performed after the washing nozzle 201 stops the operation of discharging washing water so as to eliminate the time difference.

The aforementioned high-pressure washing water denotes hydraulic pressure in a range from five times to twenty times the normal hydraulic pressure of washing water. Even though high-pressure washing water is applied to the reagent probe 7a, washing water discharged from the washing nozzle 201 plays a role as a lid with respect to the throttle portion 301, and thus, the high-pressure washing water does not scatter from the throttle portion 301. If a washing effect is enhanced by washing the reagent probe 7a with high-pressure water, as a result, an effect of a reduction in washing time or an effect of removing a reagent adhered onto the side surface of the probe 7a are improved, thereby leading to a reduction of carried over reagents. Thus, it is possible to achieve a quicker operation of the automatic analysis device which includes the reagent probe 7a.

In addition, as illustrated in FIG. 3A, by forming the channel throttle portion 304 in the channel through which washing water discharged from the washing nozzle 201 reaches the overflow 222, there is provided a structure in the throttle portion 301 in which washing water discharged from the washing nozzle 201 is accumulated. As washing water is accumulated therein, a stream of washing water increases in thickness, and thus, the washing range of the probe 7a can be widened. Accordingly, it is possible to eliminate the risk of scattering of washing water from the throttle portion 301 under circumstances of reduced washing time and washing with high-pressure water.

Here, descriptions will be given regarding operations of discharging washing water performed through the washing nozzles 201 to 203, and mechanisms of operations of suctioning performed through the vacuum nozzles 211 to 213.

FIG. 7 is a diagram illustrating an example of a mechanism for performing operations of suctioning the vacuum nozzles 211 to 213, and FIG. 8 is a diagram illustrating another example of the mechanism for performing operations of suctioning the vacuum nozzles 211 to 213.

In FIG. 7, the vacuum nozzles 211 to 213 are connected to an electromagnetic valve 240, a vacuum tank 241, and a vacuum pump 242 via tubes. Vacuum suctioning of the vacuum tank 241 is performed by the vacuum pump 242. As the electromagnetic valve 240 opens, the vacuum nozzles 211 to 213 perform vacuum suctioning with respect to the inside of the washing tank 32.

A difference between the example illustrated in FIG. 7 and the example illustrated in FIG. 8 is that a vacuum bin 250 is arranged between the electromagnetic valve 240 and the vacuum nozzles 211 to 213, in FIG. 8. Both the examples in FIGS. 7 and 8 can be applied with the present invention.

FIG. 9 is a diagram illustrating an example of a mechanism for performing operations of discharging washing water through the washing nozzles 201 to 203, and FIG. 10 is a diagram illustrating another example of the mechanism for performing operations of discharging washing water through the washing nozzles 201 to 203.

In FIG. 9, the washing nozzle 201 is connected to an electromagnetic valve 262, a low pressure pump 264, and a system water tank 265 via a tube.

In addition, the washing nozzles 202 and 203 are connected to an electromagnetic valve 261, a high pressure pump 263, and the system water tank 265 via tubes.

In the example illustrated in FIG. 9, discharge pressure of washing water from the washing nozzles 202 and 203 is set to high pressure, and discharge pressure of washing water from the washing nozzle 201 is set to low pressure.

In addition, in FIG. 10, the washing nozzles 201 and 203 are connected to the electromagnetic valve 262, the low pressure pump 264, and the system water tank 265 via tubes.

In addition, the washing nozzle 202 is connected to the electromagnetic valve 261, a high pressure pump 263, and the system water tank 265 via a tube.

In the example illustrated in FIG. 10, discharge pressure of washing water from the washing nozzles 201 and 203 is set to low pressure, and discharge pressure of washing water from the washing nozzle 202 is set to high pressure.

The electromagnetic valves 240, 261, and 262, the vacuum pump 242, the high pressure pump 263, and the low pressure pump 264 are not shown in FIG. 1 but are included in the automatic analysis device as configuration mechanisms. In addition, operations of the electromagnetic valves 240, 261, and 262, the vacuum pump 242, a high pressure pump 263, and a low pressure pump 264 are controlled by the controller 21.

FIG. 2B is a perspective cross-sectional view of the washing tank 32 according to another exemplary embodiment of the present invention. In the structure thereof, the electromagnetic valve 302 is included below the waste liquid portion 221. In addition, FIG. 3B is a top view of the washing tank 32, and the cross section taken along line B-B in FIG. 3B is the cross section illustrated in FIG. 2B. The washing tank 32 is formed with the structure having the shape illustrated in FIG. 2B and another structure having a shape symmetrical to the illustrated structure. The washing tank 33 is also configured to be equivalent to the washing tank 32.

In FIGS. 2B and 3B, in order to wash the reagent probe 7a, the reagent probe 7a is lowered into the washing tank 32. Then, the reagent probe 7a passes through the opening portion 303 formed on the top surface of the washing tank 32, and the throttle portion 301 forming a circular opening, thereby being inserted into the washing tank 32. The circular opening is the opening (portion) through which the reagent probe 7a is inserted, and the opening (portion) is formed in the throttle portion 301. The opening (portion) is not necessarily circular.

The channel throttle portion 304 is formed in the opening portion 303. The throttle portion 301 includes the opening portion 303 and forms the channel through which washing water discharged from the washing nozzle 201 (the washing mechanism) flows in the horizontal direction. The washing nozzle 201 discharges washing water which flows on the top surface of the throttle portion 301. The channel width of the channel on the downstream side from the inlet port of the channel throttle portion 304 included in the throttle portion 301 is smaller than the channel width on the upstream side therefrom. It is acceptable when the channel width of the channel on the downstream side from the opening (portion) through which the reagent probe 7a is inserted is smaller than the channel width on the upstream side.

As washing water is supplied from the washing nozzle 201, and the washing water comes into contact with the reagent probe 7a, the reagent probe 7a is washed. Meanwhile, the electromagnetic valve 302 is in the open state. Then, after the reagent probe 7a is washed, the electromagnetic valve 302 below the waste liquid portion 221 is in the closed state, and the vacuum nozzles 212, 213, and 214 (a drying mechanism) connected to the washing portion 205 of the washing tank 32 start vacuum suctioning. While performing vacuum suctioning, the reagent probe 7a is lifted. The vacuum nozzles 212, 213, and 214 (the drying mechanism) performing vacuum suctioning of washing water are arranged below the throttle portion 301. In addition, the washing nozzle 201 (the washing mechanism) performs perifusion washing with washing water supplied from the washing nozzle with respect to a liquid which has scattered and adhered to the throttle portion 301.

FIG. 2B illustrates that the washing tank 32 is formed with the illustrated structure and another structure having the symmetrical shape. Another example different therefrom is illustrated as FIG. 3C. FIG. 3C is a side view of the washing tank seen from the washing nozzle 201 side.

In the structure of FIG. 2B, different from that of FIG. 2A, there is no washing nozzle arranged below the throttle portion 301, and there is no suctioning nozzle 211 arranged above the throttle portion 301. The suctioning nozzles arranged on the side surface may be arranged alternately on the right and left as shown in FIG. 3C. Even though the suctioning nozzles are arranged in a bilateral symmetry manner, there is no change in the flow velocity at the throttle portion 301 due to vacuum suctioning. However, if the inner diameter of the washing portion 205 illustrated in FIG. 2A or 2B is decreased, washing water adhered to the reagent probe 7a can be directly suctioned through the vacuum nozzles on the side surface. Moreover, if the suctioning nozzles are arranged alternately on the right and left as shown in FIG. 3C, washing water can be directly suctioned through the suctioning nozzles, thereby improving an effect of removing washing water. Therefore, it is desirable to include a plurality of suctioning nozzles 212, 213, and 214 (first suctioning nozzles) which are arranged in a perpendicular direction, and a plurality of suctioning nozzles 212B, 213B, and 214B (second suctioning nozzles) which are arranged in the perpendicular direction and are arranged at positions so as to interpose the reagent probe 7a between the suctioning nozzles (the first suctioning nozzles) and the suctioning nozzles (the second suctioning nozzles) in a state where the probe is inserted into the opening portion. It is desirable that the nozzles are arranged alternately in the perpendicular direction.

FIG. 3C illustrates that there are provided six suctioning nozzles. However, if the suctioning effect is enhanced by widening the inner diameter of the vacuum nozzle, washing water can be removed even though there is provided only one suctioning nozzle. It is possible to achieve the effect by arranging six or more washing nozzles.

In addition, even though there is no washing nozzle arranged below the throttle portion 301, a washing effect of the reagent probe 7a can be enhanced by increasing the flow velocity of a washing liquid discharged from the washing nozzle 201. As means for increasing the flow velocity, a high pressure pump 263 illustrated in FIGS. 9 and 10 may be connected to the washing nozzle 201, or a low pressure pump 264 may be connected to the washing nozzle 201. When using a low pressure pump, it is desirable that a variable throttle (not illustrated) is attached to a position between the electromagnetic valve 262 and the washing nozzle 201 and the flow velocity against the reagent probe 7a is increased when in use.

In addition, even though there is no suctioning nozzle 211 arranged above the throttle portion 301, vacuum suctioning pressure can be increased by increasing the number of the vacuum nozzles or increasing the inner diameter of the vacuum nozzle. Even though remaining washing water discharged from the washing nozzle 201 is accumulated on the top surface of the throttle portion, the washing water accumulated in the upper portion of the throttle portion 301 can be introduced to the throttle portion. When the reagent probe 7a is lifted, there is no washing water in the periphery of the throttle portion 301. Therefore, no washing water adheres to the reagent probe 7a.

In addition, washing water accumulated in the upper portion of the throttle portion 301 is not contaminated washing water. The reason is as follows. The reagent and the like adhered onto the side surface of the reagent probe 7a flows into the overflow portion 222 during the operation of lowering the reagent probe 7a. Even though the reagent probe 7a is lowered into the washing tank and stops thereat, washing water in the washing nozzle 201 is in a discharged state. Therefore, washing water is not contaminated. As a result, even though washing water accumulated in the upper portion of the throttle portion 301 is introduced to the inside of the throttle portion 301, the reagent probe 7a is not contaminated.

With reference to the time chart of an operation of washing the reagent probe 7a illustrated in FIG. 6B, descriptions will be given regarding operations of the reagent probe 7a, the washing nozzle 201, the electromagnetic valve 302, and the vacuum nozzles 212, 213, and 214.

In FIG. 6B, at a time a', the washing nozzle 201 starts discharging of washing water. Next, at a time c', the reagent probe 7a starts being lowered toward the washing tank 32 so as to be inserted into the washing tank 32. Then, at a time d', washing water is discharged from the reagent probe 7a, thereby starting internal washing for washing the inside of the reagent probe 7a. The internal washing and external washing of the probe 7a are performed simultaneously. At the timing at which the reagent probe 7a is inserted into the opening portion, the opening portion is covered with washing water. At the time d' which is a time after the probe 7a passes through the opening portion, washing water is discharged from the reagent probe 7a.

In other words, the controller causes the washing nozzle 201 to discharge washing water therethrough in a state where the opening portion for insertion of the probe is covered with washing water, and the probe is lowered toward the opening portion. After the distal end of the probe passes through the opening portion, in a state where the opening portion is covered with the washing water while the probe is lowered, washing water is discharged from the inside of the probe. In such a structure, similar to FIGS. 2A, 3A, and 6A, since washing water discharged from the washing nozzle 201 plays a role as a lid with respect to the throttle portion 301, while the distal end of the reagent probe 7a is positioned lower than the throttle portion 301, washing water for washing the inside of the reagent probe 7a does not scatter from the throttle portion 301. In addition, on account of the role as the lid, water for internal washing can be discharged in an early stage, and thus, it is possible to reduce washing time.

Next, at a time e', an operation of lowering the reagent probe 7a stops. Subsequently, at a time g', discharging of washing water through the washing nozzle 201 stops.

Next, at a time h', the electromagnetic valve 302 is in the closed state, and at a time i', the vacuum nozzles 212, 213, and 214 start suctioning of the inside of the washing tank 32. Then, at a time j', an operation of lifting the reagent probe 7a starts. Subsequently, at a time k', an operation of washing the inside of the reagent probe 7a stops. At a time l', an operation of lifting the reagent probe 7a stops, and the vacuum nozzles 212, 213, and 214 stops suctioning of the inside of the washing tank 32. Then, at a time m', the electromagnetic valve 302 is in the open state.

In other words, the controller stops the operation of lowering the reagent probe 7a, and then, the controller stops the operation of discharging a washing liquid through the washing nozzle 201 (the washing mechanism), thereby lifting the probe while performing a vacuum suctioning operation through the vacuum nozzles 212, 213, and 214 (the drying mechanisms). In this manner, on account of vacuum suctioning performed while the reagent probe 7a is lifted, the probe can be drawn out while being dried, and thus, it is possible to reduce washing time. In addition, during vacuum suctioning, since the air is in a flow intruding into the washing tank 32 from the outside via the opening portion of the throttle portion 301, washing water adhered to the outer portion of the probe can be relegated to the distal end side of the probe. Therefore, it is possible to generate a suctioning force of the vacuum nozzle and a flow of the air enhancing a drying effect. Moreover, on account of the intruding flow of the air, water for internal washing of the probe can be prevented from scattering from the throttle portion 301. Accordingly, the inside of the reagent probe 7a can be washed for a long period of time from the lowering of the probe 7a to the lifting thereof, and thus, the reagent probe 7a can be effectively washed.

In addition, the controller stops washing water discharged from the inside of the probe after the probe 7a is lifted and before the distal end of the probe 7a passes through the opening portion. Accordingly, water for internal washing can be prevented from scattering above the throttle portion 301.

In addition, the controller causes the probe 7a to be lifted after starting a vacuum suctioning operation through the vacuum nozzles 212, 213, and 214 (the drying mechanisms) and after a predetermined period of time (a period of time between the time i' and the time j') has elapsed. On account of the vacuum suctioning operation, washing water which is discharged from the washing nozzle 201 and plays the role as a lid is suctioned below the throttle portion 301, and thus, the throttle portion 301 can be dried within the aforementioned predetermined period of time. After being dried, the outside of the probe can be dried more effectively by lifting the probe 7a. As washing water stops being discharged through the washing nozzle 201, washing water from the throttle portion 301 flows downward due to gravity. However, when vacuum suctioning is not performed, it takes time for the opening portion to be dried due to the narrow clearance between the probe and the opening portion. Meanwhile, the aforementioned time can be reduced by performing the vacuum suctioning operation before drying the throttle portion 301. In other words, the vacuum nozzles 212, 213, and 214 (the drying mechanisms) also plays a role for promptly drying the throttle portion 301 in addition to the role for drying the outside of the probe.

Another operation illustrated in FIG. 6B is also executed by a command from the controller 21 in accordance with a program stored in the controller 21.

In FIG. 3B, similar to FIG. 3A, the throttle portion 301 forms the channel through which washing water discharged from the washing nozzle 201 flows in the horizontal direction. The channel width of the channel on the downstream side from the opening portion is smaller than the channel width on the upstream side therefrom. Accordingly, washing water is likely to be accumulated in the opening portion, and thus, the opening portion can be effectively covered with washing water. In other words, it is possible to promptly carry out the role as a lid of a liquid preventing washing water for washing the inside of the probe from scattering from the throttle portion 301, or it is possible to form a thicker lid with the same volume of water discharged.

FIG. 11 is a diagram illustrating a modification example of the washing tank 32. On the right side in FIG. 11, an enlarged portion of the throttle portion 301 is illustrated. In this manner, when the shape of the opening formed by the throttle portion 301 is caused to be a mortar shape, washing water discharged from the washing nozzle 201 can be accumulated in a mortar-shaped place. As a result, similar to the above-described case, washing water can be prevented from scattering. Here, the mortar shape denotes a shape of which the opening diameter of the opening portion formed by the throttle portion decreases from the upper portion toward the lower portion.

In addition, by combining the channel which is throttled at the channel throttle portion 304 as illustrated in FIGS. 3A and 3B, and the mortar-shaped opening portion formed by the throttle portion 301 as illustrated in FIG. 11, washing water discharged from the washing nozzle 201 abuts against the mortar-shaped throttle portion 301, thereby being in a turbulent flow, and the channel is throttled at the channel throttle portion 304, thereby being in a more turbulent flow. Thus, it is possible to acquire an enhanced washing effect.

When washing water in the upper portion of the throttle portion 301 is accumulated without flowing to the overflow portion 222 after the reagent probe 7a is washed until the reagent probe 7a is lifted for removing drops of water, suctioning can be performed through the vacuum nozzle 211. Moreover, an inclination can be provided toward the overflow portion 222 so as to shape the upper portion of the throttle portion 301 in which washing water is unlikely to be accumulated.

In addition, without providing the vacuum nozzle 211, washing water adhered to the reagent probe 7a can be removed by lowering a range of the reagent probe 7a wetted by washing water from the washing nozzle 201 again compared to the throttle portion 301 after the reagent probe 7a is washed, or performing vacuum suctioning simultaneously with lowering thereof. Thus, washing water in the vicinity of the throttle portion 301 can be removed.

Moreover, washing water adhered to the reagent probe 7a can be removed by executing vacuum suctioning after the reagent probe 7a is washed, removing washing water within the range of the reagent probe 7a which is wetted due to washing water in the washing nozzle 201, and performing vacuum suctioning after lowering the range washed through the washing nozzle 201 of the reagent probe 7a again compared to the throttle portion 301.

In addition, as illustrated in FIG. 11, a washing nozzle 204 can be added.

In addition, if the washing nozzles 202, 203, and 204, and the vacuum nozzles 212 and 213 are arranged so as to be projections protruding into the washing tank 32, washing water discharged from the washing nozzle 202 which is at a position above the washing tank 32 is in a turbulent flow in which distribution of the flow velocity is generated by being centered around the reagent probe 7a inserted into the washing tank 32, thereby dripping down. Therefore, without providing projections, a washing effect can be improved compared to a case where washing water is dripped or spouted from the upper portion toward the reagent probe 7a. No matter how washing water adhered to the sample probe 7a remains, the washing water is removed by performing vacuum suctioning through the vacuum nozzles 211 to 213 after washing water stops being discharged from the washing nozzles 202 to 204, thereby being out of the question.

In the example illustrated in FIG. 11, the positions of the washing nozzles 202 to 204 and the vacuum nozzles 211 to 213 are arranged on the right and left. However, regarding a method of the arrangement as well, an equivalent washing effect of the reagent probe 7a can be acquired even though the washing nozzles 202 to 204 and the vacuum nozzles 211 to 213 are arranged alternately, or the washing nozzles and the vacuum nozzles are vertically combined. Accordingly, there is no restriction on the arrangement between the washing nozzles and the vacuum nozzles.

In addition, if the distance between the vacuum nozzles 211 to 213 and the reagent probe 7a is configured to be 1 mm or less when the reagent probe 7a is inserted into the washing tank 32, washing water adhered onto the side surface of the reagent probe 7a can be directly suctioned. Accordingly, if vacuum suctioning is performed at all times while the reagent probe 7a is lifted, washing water adhered to the reagent probe 7a is directly suctioned. Moreover, a blowing effect can be acquired by the throttle portion 301. An adhesion removal effect of washing water in accordance with the above-described configuration is unconditional, and thus, it is possible to minimize adhesion of washing water.

As described above, according to the configuration in the exemplary embodiment of the present invention, washing water is supplied from the washing nozzle 201 to the throttle portion 301 of the washing tank 32 so as to wash the throttle portion 301, and droplets adhered to the throttle portion 301 and the reagent probe 7a which have been washed are suctioned through the suctioning nozzle 211. Therefore, it is possible to realize the automatic analysis device including a washing device in which processes of the probe from washing to drying are carried out in the same washing tank, and adhesion of a liquid with respect to the washed probe can be avoided when being drawn out from the opening portion of the washing tank 32.

Moreover, according to the configuration in the exemplary embodiment of the present invention, the reagent probe 7a is inserted into the washing tank 32. While performing the lowering operation, a washing operation of the inside of the probe 7a is performed. Simultaneously, washing of washing the outside of the probe 7a is executed through the washing nozzles 201 to 203. Even when the reagent probe 7a is lifted, a drying operation is performed through the vacuum nozzles 211 and 212. Thus, washing and drying operations of the reagent probe 7a can be sped up and can be performed in a short period of time.

In the example illustrated in FIG. 2A, the washing nozzle 203 and the vacuum nozzles 212 and 213 are attached to the side surface of the washing tank 32 so as to be angulated in place of being perpendicular thereto. However, regarding the attachment angle, the necessary performance can be acquired whether the nozzles are positioned to be angulated or to be horizontally arranged.

For example, regarding the arrangement of the vacuum suctioning nozzles 211, 212, and 213, the number of nozzles can be arranged alternately and diagonally, or the speed of the air flow intruding from the throttle portion 301 can vary by increasing the number of the vacuum suctioning nozzles. Thus, there is no limitation on the attachment angle.

The number of the washing nozzles arranged in the lower portion of the throttle portion 301 is set to two in the example illustrated in FIG. 2A, and the number is set to three in the example illustrated in FIG. 11. However, even though the number of the washing nozzles in the arrangement varies such as one washing nozzle from a high pressure pump, or two or three washing nozzles from a low pressure pump, it is possible to acquire a required washing effect.

In addition, the inside of the washing tank 32 in which the washing nozzles and the vacuum nozzles in the lower portion of the throttle portion 301 are arranged may have a cylindrical shape or a square shape to be used.

In addition, the washing tank 32 of the present invention has been described related to the reagent probe 7a. However, there is a dispensing method in which the sample probe 11a is thrust deep inside a specimen of the sample container 15 and a sample is suctioned from the bottom of the sample container 15. In this case, the washing range of the sample probe 11a covers a wide range. Therefore, the washing tank of the present invention is not limited only to washing of the reagent probe. It is effective when used for washing a probe such as a sample probe which requires washing over a wide range.

The suctioning nozzle 211 and the washing nozzle 201 configure a first washing and drying mechanism. The vacuum nozzles (the suctioning nozzles) 212 and 213 and the washing nozzles 202 and 203 configure a second washing and drying mechanism.

REFERENCE SIGNS LIST

1 . . . reaction disk; 2 . . . reaction container; 3 . . . washing mechanism; 4 . . . spectrophotometer; 5, 6 . . . stirring mechanism; 7, 8 . . . reagent dispensing mechanism; 7a . . . reagent probe; 9 . . . reagent disk; 10 . . . reagent bottle; 10a . . . detergent bottle; 11 . . . sample dispensing mechanism; 11a . . . sample probe; 13 . . . washing tank; 15 . . . sample container; 16 . . . rack; 17 . . . sample transportation mechanism; 18 . . . reagent syringe; 19 . . . sample syringe; 20 . . . washing pump; 21 . . . controller; 30, 31 . . . stirring mechanism washing tank; 32, 33 . . . reagent dispensing mechanism washing tank; 201, 202, 203, 204 . . . washing nozzle; 205 . . . washing portion; 211, 212, 213, 214 . . . suctioning nozzle (vacuum nozzle); 221 . . . waste liquid portion; 222 . . . overflow portion; 240, 261, 262 . . . electromagnetic valve; 241 . . . vacuum tank; 242 . . . vacuum pump; 263 . . . high pressure pump; 264 . . . low pressure pump; 265 . . . system water tank; 301 . . . throttle portion; 302 . . . electromagnetic valve; 303 . . . opening portion; 304 . . . channel throttle portion

The invention claimed is:

1. An automatic analysis device comprising:
a probe that suctions a reagent or a sample and discharges the reagent or the sample into a reaction container;
a dispensing mechanism that moves the probe vertically and horizontally;
a suctioning and discharging mechanism that causes the probe to suction the reagent or the sample and discharges the reagent or the sample into the reaction container;
a photometer that analyzes the sample in the reaction container;
a washing tank including a throttle portion that forms an opening portion into which the probe is inserted, and where the throttle portion and the opening portion are disposed on a top surface of the washing tank;
a washing mechanism that discharges washing water above the throttle portion which flows on a top surface of the throttle portion;
an overflow portion in which the washing water discharged from the washing mechanism flows down by passing over the opening portion without dripping therein;
a drying mechanism that is arranged below the throttle portion and performs vacuum suctioning of washing water below the throttle portion; and
a controller that is configured to control operations of the dispensing mechanism, the suctioning and discharging mechanism, the washing mechanism, and the drying mechanism,
wherein the controller is further configured to cause the probe to be lowered toward the opening portion in a state where the opening portion is covered with the washing water while the washing water is discharged from the washing mechanism, and to further cause, after a distal end of the probe has passed through the opening portion, internal washing water to be discharged from inside of the probe in a state where the opening portion is covered with the washing water while the probe is lowered through the opening portion into the washing tank.

2. The automatic analysis device according to claim 1, wherein the throttle portion forms a channel where a channel width of the channel on a downstream side from the opening portion is smaller than a channel width of the channel on an upstream side therefrom.

3. The automatic analysis device according to claim 1, wherein the opening portion formed by the throttle portion has a shape in which a diameter of the opening portion decreases from an upper side toward a lower side thereof.

4. The automatic analysis device according to claim 1, wherein the controller is further configured to cause the washing mechanism to stop discharging the washing water after stopping an operation of lowering the probe through the opening portion, and cause the probe to be lifted while the drying mechanism performs the vacuum suctioning operation.

5. The automatic analysis device according to claim 4, wherein the controller is further configured to cause the washing water to stop being discharged from the probe after the probe is lifted and before the distal end of the probe is removed through the opening portion.

6. The automatic analysis device according to claim 1, wherein the drying mechanism includes:
a plurality of first suctioning nozzles which are arranged along a length of the washing tank, and
a plurality of second suctioning nozzles which are arranged along the length of the washing tank, and
wherein the first suctioning nozzles and the second suctioning nozzles are arranged alternately on opposite sides of the washing tank.

7. The automatic analysis device according to claim 1, further comprising:
an electromagnetic valve disposed below a waste liquid portion of the washing tank, and
wherein the controller is further configured to cause the electromagnetic valve to be in an open state while the probe is washed with the washing water discharged from the washing mechanism, cause the electromagnetic valve to shift from the open state to a closed state after the probe is washed with the washing water discharged from the washing mechanism, and cause the drying mechanism to start the vacuum suctioning after the electromagnetic valve is in the closed state.

8. The automatic analysis device according to claim 1, further comprising:
a valve which is controlled by the controller,
wherein a waste liquid portion is disposed on a bottom surface of the washing tank and the valve is connected to the waste liquid portion, and
wherein the controller is further configured to cause the valve to close prior to causing the drying mechanism to perform vacuum suctioning.

* * * * *